United States Patent [19]

Lewis et al.

[11] Patent Number: 5,231,158
[45] Date of Patent: Jul. 27, 1993

[54] ONE PART HEAT CURABLE ORGANOPOLYSILOXANE COMPOSITIONS AND METHOD

[75] Inventors: Larry N. Lewis, Scotia; Chris A. Sumpter, Clifton Park, both of N.Y.

[73] Assignee: General Electric Company, Schenectady, N.Y.

[21] Appl. No.: 889,579

[22] Filed: May 28, 1992

Related U.S. Application Data

[63] Continuation of Ser. No. 590,746, Oct. 1, 1990, abandoned.

[51] Int. Cl.⁵ ............................................. C08G 77/06
[52] U.S. Cl. ...................................... 528/15; 528/25; 528/31; 556/479; 556/480
[58] Field of Search ........................... 528/15, 31, 25; 556/479, 480

[56] References Cited

U.S. PATENT DOCUMENTS

| | | | |
|---|---|---|---|
| 4,849,491 | 7/1989 | Ogawa et al. | 528/15 |
| 4,906,721 | 3/1990 | Weitemeyer et al. | 528/29 |
| 5,081,199 | 1/1992 | Okinoshima | 528/15 |

FOREIGN PATENT DOCUMENTS

| | | |
|---|---|---|
| 0352493 | 1/1990 | European Pat. Off. . |
| 2282450 | 8/1975 | France . |
| 2339650 | 1/1987 | France . |
| 1042450 | 9/1966 | United Kingdom . |

OTHER PUBLICATIONS

Preparation of Poly(dimethylsiloxane) Macromonomers Having Ethynylene Functionality by the "Initiator Method", T. Suzuki and P. Y. Lo, American Chemical Society (1991) pp. 460-463.

Chemical Patents Index, Documentation Abstracts Journal-A Plastics, Polymers Week 90128, issued Sep. 5, 1990-Derwent Publications (3 pages).

*Primary Examiner*—Melvyn I. Marquis
*Attorney, Agent, or Firm*—William A. Teoli; William H. Pittman

[57] ABSTRACT

Alkynyl substituted organopolysiloxanes having alkynyl radicals attached to silicon by carbon-silicon bonds can be used in combination with a hydride siloxane crosslinker and a Group 8-10 catalyst to make one part heat curable organopolysiloxane compositions.

10 Claims, No Drawings

ONE PART HEAT CURABLE ORGANOPOLYSILOXANE COMPOSITIONS AND METHOD

This application is a continuation of application Ser. No. 07/590,746, filed Oct. 1, 1990, which is now abandoned.

BACKGROUND OF THE INVENTION

The present invention is directed to the synthesis of organopolysiloxanes having alkynyl radicals attached to silicon by carbon-silicon linkages and to their use. More particularly, the present invention relates to heat curable organopolysiloxane compositions utilizing alkynyl substituted organopolysiloxanes in combination with a hydride siloxane crosslinker and a Group 8-10 metal catalyst, such as a platinum catalyst.

Prior to the present invention, as shown by European patent application 0352493, one part heat curable thermosetting organosiloxane compositions were provided using an organopolysiloxane, a micro encapsulated hydrosilylation catalyst, an organohydrogenpolysiloxane and inhibitor in the form of compounds having at least one alkynyl group, such as an acetylenic alcohol. One part heat curable organopolysiloxanes are also shown by Weitemeyer et al, U.S. Pat. No. 4,906,721 having an organopolysiloxane with acetylenic groups attached to silicon by carbon-oxygen-silicon linkages, organopolysiloxanes with SiH groups and a platinum catalyst in the form of a platinum complex. The organopolysiloxanes compositions provided by Weitemeyer et al also have a room temperature stability of about 7 days and cure rapidly at elevated temperatures. Even though the cure of the Weitemeyer et al organopolysiloxane compositions having alkynyloxy groups joined to silicon by carbon-oxygen-silicon linkages is inhibited, these organopolysiloxanes are inherently hydrolytically unstable. As a result, the shelf stability of one part heat curable mixtures containing such hydrolytically unstable organopolysiloxane can be adversely affected. Improvement in the shelf stability of such one part heat curable organopolysiloxane compositions can be achieved, if the alkynyl substituted organopolysiloxanes are freshly prepared prior to mixing with the platinum catalyst and crosslinker.

SUMMARY OF THE INVENTION

The present invention is based on the discovery that alkynyl substituted organopolysiloxanes having alkynyl radicals of the formula, $$RC \equiv C- \tag{1}$$

attached to silicon by carbon-silicon linkages have an indefinite shelf-life at ambient temperatures, where R is a member selected from the class consisting of $C_{(1-13)}$ monovalent hydrocarbon radicals, $C_{(1-13)}$ monovalent hydrocarbon radicals substituted with radicals inert during equilibration or condensation, and $(R^1)_3Si$, and $R^1$ is selected from $C_{(1-13)}$ monovalent hydrocarbon radicals.

The alkynyl substituted organopolysiloxanes having alkynyl radicals of formula (1) can be made by effecting reaction between a halo substituted organosiloxane and an organo metallic reagent, such as an alkali metal, or alkaline earth metal organic halide for example, an acetylide substituted Grignard reagent. A typical reaction can involve contact between an acetylide substituted alkali metal, or halo alkaline earth metal of the formula, $$RC \equiv CQ \tag{2}$$

and a halo substituted organosiloxane of the formula, $$(X)_a \overset{(R^2)_b}{\underset{|}{Si}} O_{\frac{(4-a-b)}{2}} \tag{3}$$

where R is are as previously defined, $R^2$ is a member selected from the class consisting of $C_{(1-13)}$ monovalent hydrocarbon radicals and $C_{(1-13)}$ monovalent hydrocarbon radicals substituted with radicals inert during equilibration and condensation, Q is an alkali metal selected from sodium, potassium or lithium, or an alkaline earth metal halide, such as magnesium bromide, X is a halogen radical such as chloro, a is equal to 0.001 to 3, b is equal to 0 to 2, and the sum of a+b is equal to 1.8 to 3.

STATEMENT OF THE INVENTION

There is provided by the present invention, a one part heat curable organopolysiloxane compositions comprising by weight, (A) 100 parts of an alkynyl substituted organopolysiloxane having the formula, $$(RC \equiv C)_c \overset{(R^2)_d}{\underset{|}{Si}} O_{\frac{(4-c-d)}{2}} \tag{4}$$

(B) 0.2 to 10 parts of a hydride siloxane crosslinker and, (C) an effective amount of a Group 8-10 metal catalyst, where R and $R^2$ are as previously defined, c is equal to 0.001 to 2.25, d is equal to 0 to 2.25 and the sum of c+d is equal to 1.8 to 2.25.

In a further aspect of the present invention, there is provided alkynyl substituted organopolysiloxanes having the formula, $$(RC \equiv C)_a \overset{(R^2)_b}{\underset{|}{Si}} O_{\frac{(4-a-b)}{2}} \tag{5}$$

where R, $R^2$, a and b are as previously defined.

The alkynyl substituted organopolysiloxanes of formula (5) preferably consist essentially of about 0.001 to about 12 mole % of alkynyl siloxy units of the formula, $$(RC \equiv C)_e \overset{(R^2)_f}{\underset{|}{Si}} O_{\frac{(4-e-f)}{2}} \tag{6}$$

condensed with 0 to 99.999 mole % of organosiloxy units of the formula, $$(R^2)_g SiO_{\frac{(4-g)}{2}}$$

where R and $R^2$ are as previously defined, e is an integer equal to 1 to 3, inclusive, f is a whole number equal to 0 to 3 inclusive, and g is an integer equal to 1 to 3 inclusive.

Radicals included within R of formulas 1,2 and 4-6 are preferably methyl, phenyl and trimethylsilyl. Radicals included within $R^1$ are for example, methyl, phenyl and a mixture thereof. Radicals included within $R^2$ of formulas 3-6 are preferably $C_{(1-8)}$ alkyl radicals, such as methyl, ethyl, propyl; alkenyl radicals such as vinyl; $C_{(6-13)}$ aromatic radicals such as phenyl, tolyl and xylyl and substituted R radicals, such as trifluoropropyl and chlorophenyl.

Some of the halo substituted organosiloxanes included within formula (3) can be made by equilibrating a mixture of a diorganodihalosilane, such as dimethyldichlorosilane and a cyclotetrasiloxane for example octamethylcyclotetrasiloxane in the presence of an equilibration catalyst, such as Filtrol-20 (sulfuric acid supported on clay from Harshaw Filtrol of the Engelhard Corp. of Menlo Park, N.J.).

Hydride siloxane crosslinkers which can be utilized in the practice of the present invention consists essentially of a mixture of a linear hydride polysiloxane having the formula,

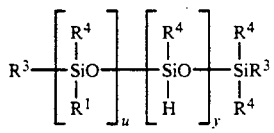

and a cyclic hydride polysiloxane having the formula,

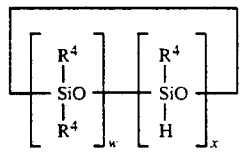

where $R^3$ is a member selected from the class consisting of hydrogen, $C_{(1-8)}$ alkyl radicals, $C_{(1-8)}$ halo substituted alkyl radicals, $C_{(6-14)}$ aryl radicals, and halo substituted $C_{(6-14)}$ aryl radicals, $R^4$ is a member selected from the class consisting of $C_{(1-8)}$ alkyl radicals, $C_{(6-14)}$ aryl radicals, $C_{(6-14)}$ halo aryl radicals and $C_{(3-8)}$ fluoroalkyl radicals, u and y are integers which can vary sufficiently to provide a hydride polysiloxane having a viscosity of from about 5 to about 10,000 centipoise at 25° C., w is an integer having a value of 0 to 5 inclusive, x is an integer having a value of from 1 to 8 inclusive and the sum of w and x has a value of from 3 to 8 inclusive. Preferably, the hydride siloxane cross-linker consists essentially of chemically combined organosiloxy units having silicon bonded hydrogen atoms attached to silicon to form the polysiloxane chain backbone. Preferably, the cyclic hydride polysiloxane is a mixture of cyclic hydride polysiloxane within the above formula.

Group 8-10 metal catalysts which can be used in the practice of the present invention are preferably platinum. However, rhodium, ruthenium, iridium, cobalt, and nickel catalysts also have been found effective. Platinum catalysts which are preferred are, for example, reaction products of an olefin and chloroplatinic acid as described in Ashby, U.S. Pat. No. 3,159,601, or the reaction product of platinic chloride and cyclopropane as described in Ashby, U.S. Pat. No. 3,159,662. Further platinum complexes which can be used as the platinum catalyst are reaction products of chloroplatinic acid with up to 2 moles, per gram of platinum of a member selected from the class consisting of alcohols, ethers, aldehydes and mixtures thereof, as shown in Lamoreaux, U.S. Pat. No. 3,220,972. The preferred platinum catalyst is shown by Karstedt, U.S. Pat. No. 3,775,452, which is formed by reacting chloroplatinic acid with tetramethyldivinyldisiloxane in the presence of sodium bicarbonate in an ethanol solution. It has been found that effective results can be achieved if sufficient platinum catalyst is employed in the heat curable organopolysiloxane compositions of the present invention to provide from 1 to 250 parts of platinum, and preferably from 1 to 200 parts of platinum, per million parts of heat curable mixture.

The heat curable organopolysiloxane compositions also can contain from 0 to 50 parts by weight of a filler, per hundred parts of heat curable composition. It is preferred in instances where the alkynyl substituted organopolysiloxane is a polydiorganosiloxane, to use extending fillers or reinforcing fillers, such as fumed silica. Precipitated silica also can be used in instances where it is desired to increase the physical properties such as the tensile strength and tear strength of cured products obtained from the resulting heat curable mixture. Other extending fillers which may be utilized are, for example, titanium dioxide, lithopone, zinc oxide, zirconium silicate, silica airogel, iron oxide, diatomaceous earth, calcium carbonate, glass fibers, magnesium oxide, chromic oxide, zirconium oxie, aluminum oxide, α-quartz, clay, carbon, and graphite. In order to minimize the viscosity increase generally experienced when using reinforcing fillers, the reinforcing fillers can be heat treated with cyclic polysiloxanes or silazanes. Another filler which can be used in the practice of the present invention is ground quartz which has been found to enhance the burn-resistant properties of cured products obtained from the heat curable organopolysiloxanes.

The heat curable organopolysiloxane compositions of the present invention can be used as paper release compositions on substrates, such as plastic and paper. In addition, the heat curable organopolysiloxane compositions can be used as gasket material applied by liquid injection molding methods, conformal coatings for electronic devices, pressure sensitive adhesives and cured gels for use as bumpers or shock absorbers in automotive applications.

The alkynyl substituted organosiloxanes of the present invention are preferably made by effecting reaction between a halo substituted organosiloxane, such as a chlorine endstopped polydimethylsiloxane, and a substituted acetylide Grignard reagent, such as a phenylacetylene magnesium bromide. Procedures for preparing the acetylide Grignard agents are for example, reacting phenylacetylene in a dry diethylether solution at 0° C. with ethyl magnesium bromide.

In order that those skilled in the art will be better able to practice the present invention, the following examples are given by way of illustration and not by way of limitation. All parts are by weight.

EXAMPLE 1

There was added at 10° C. 4.40 grams ($3.41 \times 10^{-2}$ mol) of dimethyldichlorosilane followed by 3.50 grams (3.0 wt %) of activated Filtrol-20 to 123.75 grams ($4.17 \times 10^{-1}$ mol) of octamethylcyclotetrasiloxane. After 30 minutes at 10° C., the reaction mixture was heated at 80° C. for 18 hours. The reaction was then cooled to room temperature, diluted with 500 ml of methylenechloride and filtered through a two inch pad of celite with suction. The celite was washed with methylene chloride and the methylene chloride was removed in vacuo from the equilibrated siloxane fluid. The resulting chlorine endstopped dimethylsiloxane fluid ($D_p = 110$) was stripped at 150° C. at 0.15 mm Hg. There was added a 5% excess ($9.33 \times 10^{-3}$ mol) of phenylacetylene magnesium bromide to 36.74 grams ($4.4 \times 10^{-3}$ mol) of the chlorine endstopped dimethylsiloxane fluid in 1 L of dry ethyl ether. The phenylacetylene magnesium bromide was made from phenylacetylene added dropwise at 0° C. to a dry diethylether solution of ethyl magnesium bromide over 2 hours. After the addition, the reaction mixture was heated to reflux for 0.5 hours then stirred at room temperature for 12 hours. The resulting mixture was then washed with $2 \times 500$ ml of water, $1 \times 500$ ml of saturated sodium chloride, dried over sodium sulfate and concentrated under reduced pressure to give a very light yellow fluid. Based on $^1$H and $^{13}$C NMR and method of preparation, the product was a phenylacetylene endcapped polydimethylsiloxane having an average of about 110 dimethylsiloxy units and endcapped with phenylacetylide units attached to silicon by carbon-silicon linkages. $^1$H NMR: δ 7.50 (2H, dd, 7.32 (8H, m) 2.33 (12H, s) 0.07 (648, s)ppm; $^{13}$C NMR δ 131.4(4C), 128.0 (2C), 127.6 (2C), 127.5 (4C), 104 (2C), 82.7 (2C), 0.33 (220C) ppm.

A heat curable organosiloxane composition was prepared by adding 25 parts per million of platinum in the form of a platinum vinyl siloxane to 100 parts of the alkynyl endstopped polydimethylsiloxane fluid. The mixture was stirred for approximately 1 minute then there was added 2.5 parts of a hydride siloxane crosslinker in the form of a copolymer of polydimethylsiloxane polyhydrogen methylsiloxane, $MD_xD_y^HM$, having 0.8 weight % hydrogen and a viscosity of 150 cps. The resulting formulation was mixed for approximately 2 minutes.

A similar procedure was followed to prepare a trimethylsilylacetylene endstopped polydimethylsiloxane which was used to prepare another curable polydimethylsiloxane. The room temperature stability of these heat curable organopolysiloxanes under ambient conditions and their cure rates at 150° C. were evaluated using a Sunshine gel timer. The following results were obtained:

|  | 150° C. Cure (sec) | Room Temperature Stability (days) |
| --- | --- | --- |
| phenylactylene | 2145 | 7 |
| trimethylsilylacetylene | 2321 | 11 |

The above results show that one part heat curable organopolysiloxane compositions can be made in accordance with the practice of the invention. The one part compositions have satisfactory shelf stability at ambient temperatures. In addition, a satisfactory cure of the compositions were effected at 150° C. The one part compositions can be used as an adhesive coating on various substrates, such as paper or plastic.

EXAMPLE 2

Trimethylsilylacetylene magnesium bromide was made by adding phenylacetylene dropwise over a 2 hour period to an anhydrous ethyl ether solution of ethyl magnesium bromide at 0° C. The trimethylsilylacetylene magnesium bromide (0.2 mol, 2% excess) was then added to 10 g ($3.51 \times 10^{-2}$ mol) of hexachlorodisiloxane in 300 ml of anhydrous ethyl ether. After the addition, the reaction mixture was heated to reflux for 0.5 hours, then stirred at room temperature for 12 hours. The resulting mixture was then washed with $2 \times 500$ ml water, $1 \times 500$ ml saturated sodium chloride, dried over magnesium sulfate and concentrated under reduced pressure to give a semi-solid mass. This material was then recrystallized from hot hexane to give a crystalline solid. Based on $^1$H, $^{13}$C NMR and method of preparation, the product was hexakis(trimethylsilylacetylene)disiloxane. $^1$H NMR: δ 0.17 (s) ppm; $^{13}$C NMR: δ 116.9 (6C), 103.8 (6C), −0.56 (18C) ppm; mp=163°-164° C.

A heat curable organosiloxane composition was prepared by adding 25 parts per million of platinum in the form of a platinum divinyltetramethyldisiloxane complex to 100 parts of polydimethylsiloxane fluid with dimethylvinylsiloxy end groups (4% by weight of vinyl group in relation to polymer weight) having a viscosity of 400 cps at 25° C. and 0.25 parts of hexakis(trimethylsilylacetylene)disiloxane as an inhibitor. The resulting mixture was stirred for approximately 2 minutes. There was then added 2.5 parts of a hydride siloxane crosslinker in the form of a copolymer of polydimethylsiloxane polyhydrogen methylsiloxane, $MD_xD^H_yM$, having 0.8% by weight hydrogen and a viscosity of 150 cps. The resulting formulation was mixed for approximately 2 minutes. The resulting one part heat curable organopolysiloxane mixture gelled within 60 minutes at ambient temperatures. A similar heat curable one part formulation gelled in less than one minute when the hexakis(trimethylsilylacetylene)disiloxane inhibitor was excluded.

Although the above examples are directed to only a few of the very many variables which can be employed in making the heat curable organopolysiloxane compositions of the present invention, it should be understood that the present invention is directed to the use of a much broader variety of acetylene substituted organopolysiloxanes, Group 8-10 metal catalysts and hydride siloxane crosslinkers, as set forth in the description preceding these examples.

What is claimed is:
1. A one part heat curable organopolysiloxane compositions comprising by weight,
(A) 100 parts of an alkynyl substituted organopolysiloxane having the formula,

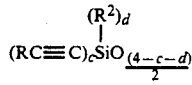

(B) 0.2 to 10 parts of a hydride siloxane crosslinker and,
(C) an effective amount of a Group VIII metal catalyst, where R is a member selected from the class consisting of $C_{(1-13)}$ monovalent hydrocarbon radicals, $C_{(1-13)}$ monovalent hydrocarbon radicals substituted with radicals inert during equilibration or condensation, and $(R^1)_3Si$, $R^1$ is selected from $C_{(1-13)}$ monovalent hydrocarbon radicals, $R^2$ is a member selected from the class consisting of $C_{(1-13)}$ monovalent hydrocarbon radicals and $C_{(1-13)}$ monovalent hydrocarbon radicals substituted with radicals inert during equilibration and condensation, c is equal to 0.001 to 2.25, d is equal to 0 to 2.25 and the sum of c+d is equal to 1.8 to 2.25.

2. A heat curable composition in accordance with claim 1, where (A) is a phenylacetylene endstopped polydimethylsiloxane.

3. A heat curable composition in accordance with claim 1, where (A) is a trimethylsilylacetylene endstopped polydimethylsiloxane.

4. A heat curable composition in accordance with claim 1, where the hydride siloxane crosslinker is a copolymer of condensed dimethylsiloxy units and methyl hydrogen siloxy units having 0.8 weight % hydrogen.

5. A heat curable composition in accordance with claim 1, where the platinum catalyst is a vinyl siloxane platinum complex.

6. An alkynyl substituted organopolysiloxane having the formula,

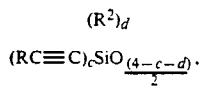

where R is a member selected from the class consisting of $C_{(1-13)}$ monovalent hydrocarbon radicals, $C_{(1-13)}$ monovalent hydrocarbon radicals substituted with radicals inert during equilibration and condensation, and $(R^1)_3Si$, $R^1$ is selected from $C_{(1-13)}$ monovalent hydrocarbon radials, $R^2$ is a member selected from the class consisting of $C_{(1-13)}$ monovalent hydrocarbon radicals and $C_{(1-13)}$ monovalent hydrocarbon radicals substituted with radicals inert during equilibration and condensation, c is equal to 0.001 to 2.25, d is equal to 0 to 2.25 and the sum of c+d is equal to 1.8 to 2.25.

7. An alkynyl substituted organopolysiloxane in accordance with claim 6, where R is phenyl or trimethylsilyl.

8. Hexakis(trimethylsilylacetylene)disiloxane.

9. A method for making alkynyl substituted organopolysiloxanes comprising effecting reaction between an acetylide substituted organometallic of the formula,

and a halo substituted organosiloxane of the formula,

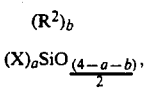

where R is a member selected from the class consisting of $C_{(1-13)}$ monovalent hydrocarbon radials, $C_{(1-13)}$ monovalent hydrocarbon radicals substituted with radicals inert during equilibration and condensation, and $(R^1)_3Si$, $R^1$ is selected from $C_{(1-13)}$ monovalent hydrocarbon radicals, $R^2$ is a member selected from the class consisting of $C_{(1-13)}$ monovalent hydrocarbon radicals and $C_{(1-13)}$ monovalent hydrocarbon radicals substituted with radicals inert during equilibration and condensation, Q is an alkali metal group selected from sodium, potassium or lithium, or an alkaline earth metal halide, X is a halogen radical, a is equal to 0.001 to 3, b is equal to 0 to 2, and the sum of a+b is equal to 1.8 to 3.

10. A method in accordance with claim 9, where the alkaline earth metal halide is magnesium bromide.

* * * * *